(12) United States Patent
Rüsing et al.

(10) Patent No.: US 8,900,831 B2
(45) Date of Patent: Dec. 2, 2014

(54) METHOD FOR THE CULTIVATION OF MICROORGANISMS OF THE GENUS THRAUSTOCHYTRIALES BY USING AN OPTIMIZED LOW SALT MEDIUM

(76) Inventors: Matthias Rüsing, Köln (DE); Markus Luy, Ried-Brig (CH)

(*) Notice: Subject to any disclaimer, the term of this patent is extended or adjusted under 35 U.S.C. 154(b) by 2221 days.

(21) Appl. No.: 10/578,968

(22) PCT Filed: Nov. 10, 2004

(86) PCT No.: PCT/EP2004/012718
§ 371 (c)(1),
(2), (4) Date: May 10, 2006

(87) PCT Pub. No.: WO2005/045003
PCT Pub. Date: May 19, 2005

(65) Prior Publication Data
US 2007/0054384 A1    Mar. 8, 2007

(30) Foreign Application Priority Data

Nov. 10, 2003  (DE) .................................. 103 52 838

(51) Int. Cl.
*C12P 7/64*   (2006.01)
*C12N 1/00*   (2006.01)

(52) U.S. Cl.
USPC ........................................ 435/134; 435/243

(58) Field of Classification Search
USPC ................................................ 435/134, 243
See application file for complete search history.

(56) References Cited

U.S. PATENT DOCUMENTS 5,340,742 A * 8/1994 Barclay ...................... 435/256.8
5,518,918 A   5/1996 Barclay
6,410,281 B1  6/2002 Barclay
6,451,567 B1  9/2002 Barclay
6,509,178 B1 * 1/2003 Tanaka et al. ................. 435/134

FOREIGN PATENT DOCUMENTS

| EP | 0823475 A1 | 2/1998 |
| WO | WO 91/07498 A1 | 5/1991 |
| WO | WO 91/11918 A1 | 8/1991 |
| WO | WO 96/33263 A1 | 10/1996 |
| WO | WO 98/03671 A1 | 1/1998 |

OTHER PUBLICATIONS

Yokochi et al. "Optimization of docosahexaenoic acid production by *Schizochytrium limacinum* SR21". Appl. Microbiol. Biotechnol. 1998, vol. 49, pp. 72-76.*
Fan et al. "Physiological studies of subtropical mangrove thraustochytrids". Botanica Marina, 2002, vol. 45, pp. 50-57.*

* cited by examiner

*Primary Examiner* — Vera Afremova

(57) ABSTRACT

The invention relates to an optimized method for cultivating microorganisms of the genus *Thraustochytriales*, according to which the microorganisms are cultivated in a low salt medium without adding sodium salts and chloride salts, the total salt content being less than 3.5 g/L (corresponding to less than 10 percent of sea water salt content), whereupon the PUFAs are isolated from the microorganisms and/or the medium. The invention especially relates to novel optimized media having a substantially reduced total salt content, above all a particularly reduced NaCl content. The production of PUFAs can be substantially improved and significantly simplified by using a novel combination of different salts as a media composition in which the overall weight ratios of ions do not exceed 1.75 g/L. Furthermore, said medium preferably contains no added sodium salt and chloride salt at all, which helps prevent environmental damages caused by wastewaters containing salt.

13 Claims, 2 Drawing Sheets

METHOD FOR THE CULTIVATION OF MICROORGANISMS OF THE GENUS THRAUSTOCHYTRIALES BY USING AN OPTIMIZED LOW SALT MEDIUM

Different PUFAs (polyunsaturated fatty acids) and particularly omega-3 fatty acids (n-3 fatty acids) are essential components of the human nutrition.

It is, however, known that in the majority of industrialized nations, the supply of n-3 fatty acids is insufficient. In contrast to that, the overall proportion of fat in the diet, as well as the intake of saturated fatty acids and n-6 fatty acids, is too high. This is due to a change in the composition of our diet, which has occurred especially in the last approx. 150 years, and which is being linked (Simopoulos, A. P., 1999, Am. J. Clin. Nutr. 70, 560-569) to the appearance of different chronic diseases of civilization, such as, for example, cardiovascular diseases—the main cause of death in industrialized nations. A great number of studies has meanwhile shown that by means of a targeted increase in the intake of n-3 fatty acids, in particular of eicosapentaenoic acid (EPA) and docosahexaenoic acid (DHA), it is possible to significantly reduce the cardiovascular risk (GISSI-Prevenzione Investigators (Gruppo Italiano per lo Studio della Sopravvivenza nell'Infarto miocardico), 1999, Dietary supplementation with n-3 polyunsaturated fatty acids and vitamin E after myocardial infarction: results of the GISSI-prevenzione trial., Lancet 354, 447-455; Burr et al., 1989, Effects of changes in fat, fish, and fiber intake on death and myocardial reinfarction: diet and reinfarction trial (DART). Lancet 2, 757-761). Accordingly, many different organizations (WHO, FAO, AHA, ISSFAL, British Nutrition Foundation, etc.) recommend a significant increase in the intake of n-3 fatty acids (Kris-Eherton et al., Fish Consumption, Fish Oil, Omega-3 Fatty Acids, and Cardiovascular Disease. Circulation 2002, 2747-2757).

Sources for the production of PUFAs and, in particular, n-3 fatty acids are above all marine cold water fish and the oils extracted therefrom, but also marine microorganisms, which, compared to fish, have the advantage that they can be used in ferments for producing PUFAs under cost effective and controlled conditions. Fermentative production does not pose any contamination risk, as is often described for fish or the fish oils extracted therefrom (Olsen S F. Int J Epidemiol. 2001:1279-80). In addition, the composition of the extracted oils can be can be positively influenced by selecting the organism and the culture conditions and is not subjected to seasonal variations, as described for fish and fish products as well (Gamez-Meza et al. Lipids 1999:639-42).

Microorganisms suitable for producing n-3 PUFA are found, for example, in bacteria of the genus *Vibrio* (e.g.: *Vibrio marinus*) or among the dinoflagellates (*Dinophyta*), there particularly the genus *Crypthecodinium*, such as *C. cohnii*, or among the *Stramenopiles*, such as *Pinguiophyceae*, e.g. *Glossomastix, Phaeomonas, Pinguiochrysis, Pinguiococcus* and *Polydochrysis*. Preferred microorganisms for the fermentative production of PUFA belong to the *Stramenopiles* (or *Labyrinthulomycota*), in particular to the order *Thraustochytriales*, (*Thraustchytriidea*) and there again, in particular, to the genera *Japonochytrium, Schizochytrium, Thraustochytrium, Althornia, Labyrinthuloides, Aplanochytrium* and *Ulkenia*.

It is known that some of the mentioned microorganisms can be used for industrial production of fatty acids and corresponding processes have been described. Accordingly, the international patent application WO 91/07498 A1 discloses the production of PUFAs using organisms of the genera *Thraustochytrium* and *Schizochytrium*. WO 91/11918 A1 discloses the production of PUFAs using *Crypthecodinium cohnii*, WO 96/33263 A1 and the corresponding European patent application EP 0 823 475 A1 describes the production of PUFAs using microorganisms of the genus *Schizochytrium*, while the patent application WO 98/03671 discloses the production of PUFAs using microorganisms of the genus *Ulkenia*.

The natural habitat of the described microorganisms and in particular of *Labyrinthulomycota* is a marine habitat. Consequently, these microorganisms are usually cultivated in salt-containing media, where, for the purpose of the present invention, the salt content of sea water is defined as 32-35 g/L and a content of 90-95% of sodium and chloride. Typical media for cultivating marine microorganisms such as *Thraustochytrium* or *Schizochytrium* are based on sea water (e.g. ATCC (American Type Culture Collection) 790 By+ medium [yeast extract 1.0 g, peptone 1.0 g, D+ glucose 5.0 g, sea water 1 L]). It is, however, also known that microorganisms of the order *Thraustochytriales* can survive in a culture medium with very low salinity. However, below a limit of 7.5-15 g salt/L, corresponding to a salinity of 7.5-15%, its growth is described as being only very low and without intermediate maximum levels in the low salinity range. Optimal growth rates are only achieved above the abovementioned salinity limit (Fan et al. Botanica Marina 45, 2002, pp. 50-57).

Reduced salt contents of about 50-60% of sea water have nonetheless been described for the commercial fermentation of euryhaline microorganisms. According to Henderson's "Dictionary of biological terms", euryhaline marine organisms are those capable of adjusting themselves to a broad range of salt contents (Henderson W. D., Lawrence, E., Henderson's dictionary of biological terms, $10^{th}$ ed. 1992, p. 173).

It has been described that euryhaline microorganisms belonging to the *Stramenopiles* (or *Labyrinthulomycota*) can produce larger quantities of PUFA in fermentation media with a reduced content in sodium ions (60% of sea water) (U.S. Pat. No. 6,451,567). Also described is the use of culture media with a low chloride content with the objective of reducing the corrosive effects of the chloride on the fermentation equipment (U.S. Pat. No. 6,410,281). This has been shown, for example, for microorganisms of the genera *Thraustochytrium* and *Schizochytrium* using fermentation media containing chloride in a concentration of less than 3 g/L (U.S. Pat. No. 5,340,742, U.S. Pat. No. 6,451,567, U.S. Pat. No. 6,410,281). It is also known that cultivation is also possible under conditions of reduced salt content compared with salt water. Particular reference is made here to the patent documents WO 98/03671 A1, EP 0 823 475 A1, U.S. Pat. No. 6,451,567, U.S. Pat. No. 6,410,281.

It is further known that for the fermentation of a microorganism of the genus *Schizochytrium* (*Schizochytrium* sp. S31; ATCC 20888) a maximum in the relative yield of fatty acids is achieved at a sodium chloride concentration of 1.75 g/L. The total amount of salt used therefor is less than 10% of the sea water salt content, but it comprises primarily sodium and chloride ions (EP 0 512 997 B1 and U.S. Pat. No. 5,518,918)

All the methods described so far do, however, have disadvantages. The effectiveness of fermentative processes is limited particularly by the attainable biomass and the product content per biomass. Furthermore, the oils produced can partly present fatty acid spectra which do not necessarily correspond with the desired products, but must be procedurally modified first. Processing is often complicated by the to some extent low product content per biomass because of the relatively large amounts of biomass needed to be processed in order to obtain relatively small product quantities. Moreover, all the methods described so far involve relatively high total salt contents in the culture media. This leads not only to massive problems during the processing of the products, but represents an extreme environmental disadvantage, since, not only large amounts of biomass, but also wastewaters containing large amounts of salt are generated, which need to be disposed of.

In the light of the state of the art, it was therefore an object of the present invention to provide a novel, simple and economic method for cultivating *Thraustochytriales* using media comprising reduced salt contents. Apart from being cost effective, the method should be easy to implement and enable the high yield production of high purity PUFAs or of PUFA containing products.

This and further not explicitly described tasks, which can, however, be derived or deduced without difficulty from the relations discussed in the introduction, are achieved by the object defined in the claims of the present invention.

An advantageous method for cultivating *Thraustochytriales* is provided by the method defined in claim 1. This method comprises the cultivation of microorganisms of the order *Thraustochytriales* in a low salt medium without adding sodium or chloride ions in solid or dissolved form, the total salt content being less than 10% in relation to sea water, i.e. a total salt content of less than approx. 3.5 g/L.

The invention further comprises a method for producing high purity PUFAs.

Preferred PUFAs are, according to the invention, DHA, DPA and EPA.

Particularly, the microorganisms cultivated by means of the abovementioned method present a production of more than 10%, preferably more than 14%, and particularly preferably more than 18% DHA per dry biomass.

Particularly, the microorganisms cultivated by means of the abovementioned method show a production of more than 5%, preferably more than 7%, and very particularly preferably more than 10% DPA per dry biomass.

The PUFAs can be obtained in high yield and purity by isolating the PUFAs from the microorganisms (biomass) and/or culture medium following the cultivation.

In addition, the present invention comprises a method for producing biomass, where the biomass is provided by the cultivation method according to the invention.

This biomass can be used in all imaginable ways. In particular, this biomass can be used, for example, in dried form (dry biomass), directly as foodstuff or animal feed.

In addition, the invention also comprises an oil type which is obtained by carrying out the cultivation method according to the invention and by isolating said oil from the microorganisms (biomass) and/or culture medium.

In particular, this is an oil type which, apart from many other preferred applications, can be advantageously used for human nutrition.

Under the conditions according to the invention, the microorganisms thereby present a production of more than 30 wt % oil, preferably of more than 35 wt % oil per unit of weight of dry biomass.

According to the invention, oil is understood to be a proportion of at least 70% neutral lipids and at least 2% phospholipids, which corresponds to the normal fatty acid spectrum of *Thraustochytriales* known to the person skilled in the art. The neutral lipids thereby comprise at least 80% triglycerides and other compounds such as diacylglycerides, sterols, etc. In addition, the triglyceride weight fraction comprises about 95% fatty acids and 5% glycerin. The possibility of fermenting a marine microorganism at such a low salt concentration, which corresponds to less than 10% of the typical sea salt content, and in particular the fact that it is possible to completely dispense with the addition of $Na^+$ and $Cl^-$ ions, which dominate in sea water and normally account for approx. 90% of the ions available in sea water, was totally surprising.

Surprisingly, not only the fermentation itself was possible, but, in addition to that, the proportion of PUFA in the biomass significantly increases when using the low salt medium according to the invention. Even more surprising is that this effect not only compensates, but even exceeds a slight decrease in the produced biomass (example 2). The proportion of the predominant PUHA DHA per dry biomass has hereby increased by more than 10% in relation to the comparative fermentation in medium 1 (50% sea water salt content). Product processing is simplified by the higher product concentration and lower contamination with salts, and all this at an overall larger space-time yield.

Until the present invention, no known fermentation process was available for the production of n-3 fatty acids in microorganisms of the order *Thraustochytriales* using a medium with such low salt concentration and with no sodium and chloride additions.

PUFAs are polyunsaturated long-chain fatty acids with a chain length>C12 comprising at least two double bonds. PUFAs which can be produced following the method according to the present invention are in particular n-3 fatty acids and n-6 fatty acids.

In the sense of the present invention, n-3 fatty acids (omega-3 fatty acid, ω-3 fatty acids) are understood to be polyunsaturated long-chain fatty acids with a chain length>C12 comprising at least two or more double bonds, where the first double bond is constituted between the carbon atoms C3 and C4 starting from the alkyl end. Accordingly, for n-6 fatty acids the first double bond is located between the carbon atoms C6 and C7 starting from the alkyl end.

Microorganisms belonging to the group of the *Labyrinthulomycota* are considered for the production of PUFAs following the method according to the present invention. Microorganisms of the order *Thraustochytriales* (*Thraustchytriidea*) are preferred (Lewis, T. E., Nichols, P. D., McMeekin, T. A., The Biotechnological Potential of Thraustochytrids, Marine Biotechnology, 1999, pp. 580-587 and Porter, D. Phylum *Labyrinthulomycota* in Handbook of protoctista: the structure, cultivation, habitats, and life histories of the eukaryotic microorganisms and their descendants exclusive of animals, plants, and fungi: a guide to the algae, ciliates, foraminifera, sprorozoa, water molds, and other protoctists. Editors: Margulis, L, Corliss, J. O., Melkonian, M. and Chapman, D. J., editorial coordinator, McKhann, H. I., Jones and Bartlett Publishers, ISBN 0-86720-052-9 1990, pp. 388-398). Particularly preferred are microorganisms of the genera *Japonochytrium, Labyrinthuloides, Aplanochytrium Althornia, Schizochytrium, Thraustochytrium* and *Ulkenia*. Of these, *Schizochytrium, Thraustochytrium* and *Ulkenia* are very particularly preferred. Particularly preferred are: *Japonochytrium* sp. ATCC 28207, *Thraustochytrium aureum* (particularly ATCC 28211 and ATCC 34304), *Thraustochytrium roseum* ATCC 28210 *Thraustochytrium* sp. ATCC 20890, ATCC 20891, ATCC 20892 and ATCC 26185, *Schizochytrium aggregatum* ATCC 28209, *Schizochytrium* sp. ATCC 20888 and ATCC 20889, *Schizochytrium* SR21, as well as *Ulkenia* sp. SAM 2179 and SAM 2180.

Microorganisms suitable for the method according to the invention are both wild type forms and mutants and strains derived therefrom as well as recombinant strains of the corresponding organisms. The present invention especially comprises mutants or recombinant strains for increasing the production of PUFA.

The microorganisms according to the present invention are cultivated by inoculating a liquid or a solid medium with a preculture of these organisms.

Culture techniques suitable for microorganisms of the order *Thraustochytriales* are well known to the person skilled in the art. Typically, but not exclusively, the culture is carried out by means of aqueous fermentation in a corresponding container. Examples for a typical container for such type of fermentation comprise shaking flasks or bioreactors, such as for example STRs (stirred tank reactors) or bubble columns. The culture is typically carried out at temperatures of between 10° C. and 40° C., preferably between 20° C. and 35° C., particularly preferably between 25° C. and 30° C., more particularly preferably between 27° C. and 29° C. and in particular at 28° C.

In a further embodiment of the present invention, the low salt medium comprises less than 1.5 g/L total salts.

In a further preferred embodiment of the present invention the total salt content of the low salt medium corresponds to a value of <15% of the salt content of sea water, preferably of <12% and particularly preferably of <10%. Very particularly preferred is a total salt content of <8% of the salt content of sea water.

No sodium salts are added to the low salt medium. No chloride salts are further added to the low salt medium according to the invention.

According to the present invention, addition is understood to mean an addition in both dissolved and solid form. For example, the addition of sea water, even in the smallest amounts, would be, according to the invention, an addition of sodium and chloride salts. The addition of unusual media components to the medium according to the invention must, if these unusual media components contain corresponding sodium or chloride ions, also be understood as addition of these salts. It is, however, clear to the person skilled in the art, that the usual (and mostly necessary, i.e. essential) media components water (tap water), yeast extract, corn steep liquor or similar comprise a very small, unavoidable own proportion of sodium and chloride. The addition of such usual media components is therefore not understood as addition of sodium and chloride salts according to the invention.

Yeast extract, for example, contains less than 2 wt % NaCl. If, for this reason, yeast extract is added to the medium in the usual amounts, i.e. between 10 and 20 g/L, the NaCl content increases by less than 0.2 g/L. This is not regarded as NaCl addition according to the invention.

In a particularly preferred embodiment, this medium is therefore free of sodium and/or chloride salt additions.

The total sodium content of the low salt medium is very particularly preferably less than 2 g/L, preferably less than 500 mg/L and very particularly preferably less than 150 mg/L. The total chloride content of the low salt medium is preferably less than 2 g/L, preferably less than 500 mg/L and very particularly preferably less than 250 mg/L.

The sum of the weight fractions of Na ions and Cl ions is particularly preferably less than 1.75 g/L.

The low salt medium further preferably comprises one or more carbon sources, as well as one or more nitrogen sources. Substances usable as carbon and nitrogen sources for cultivating microorganisms of the order *Thraustochytriales* are well known to the person skilled in the art.

Usable carbon sources are for example carbohydrates such as glucose, fructose, xylose, sucrose, maltose, soluble starch, fucose, glucosamine, dextran, glutamic acid, molasses, glycerin or mannitol or also fats and oils or vegetable hydrolysates.

Usable natural nitrogen sources are, for example, peptone, yeast extract, malt extract, meat extract, casamino acids, corn steep liquor or soy beans, usable organic nitrogen sources are, for example, glutamate and urea, but also inorganic nitrogen sources such as, for example, ammonium acetate, ammonium hydrogen carbonate, ammonium sulfate or ammonium nitrate can be used as nitrogen source.

The low salt medium can contain all other components known to the person skilled in the art to assist the cultivation of microorganisms of the order *Thraustochytriales*, in particular inorganic salts of, for example, Ca, Mg, K, Fe, Ni, Co, Cu, Mn, Mo or Zn. Phosphates such as potassium hydrogen phosphate, or carbonates such as calcium carbonate, sulfates such as ammonium sulfate, magnesium sulfate, iron sulfate or copper sulfate may be mentioned examples. Further usable inorganic salts are, for example, halogenides, such as potassium bromide or potassium iodide.

Where applicable, the medium can comprise additional macro- or micronutrients, such as amino acids, purine, pyrimidine, corn steep liquor, protein hydrolysates, vitamins (water soluble and/or water insoluble) and other media components well known to the person skilled in the art. Antifoaming agents can be added, if necessary. The medium can contain complex components or be chemically defined.

The amounts of the individual components can vary, as long as there is no negative effect on the growth or productivity of the microorganisms. The person skilled in the art can easily determine the composition for each individual case according to the requirements of the microorganism. Generally, the carbon source is added at a concentration of 50 to 300 g/L and the nitrogen source at a concentration of 1 to 30 g/L. Preferably, the nitrogen content is adjusted in dependence of the carbon content of the medium.

A particularly preferred low salt medium comprises, as the case may be, apart from other components such as, for example, nutritive components, at least one salt selected from the group comprising magnesium sulfate, calcium carbonate and potassium phosphate, where the salt(s) is/are preferably added at not more than 3 g/L each, particularly preferably at not more than 1 g/L each, without the total salt content according to the invention being exceeded. It is particularly preferred when magnesium sulfate, calcium carbonate and potassium phosphate are added to the medium.

Preferred nutritive components are glucose, yeast extract and/or corn steep liquor (CSL) in the usual quantities as well as further common nutritive components known to the person skilled in the art.

The pH value of the medium is set to a range of 3 to 10, preferably 4 to 8, particularly preferably 5 to 7, very particularly preferably 6 by adding a corresponding acid or base.

The medium is subsequently sterilized. Techniques for sterilizing media are well known to the person skilled in the art, autoclaving and sterile filtration may be mentioned as examples.

Cultivation can take place batchwise, in a fed-batch mode or continuously, as it is generally known to the person skilled in the art.

Batch or fed-batch cultivation usually takes place over a period of 1 to 12 days, preferably 2-10 days, particularly preferably 3-9 days.

The media components can be added to the low salt medium individually or as a mixture, a previously prepared mixture being also possible. The components, in particular the carbon and nitrogen source(s) or specific medium additions can be added prior to or during the cultivation. The addition can be repeated once or several times or can also take place continuously.

The produced PUFA are generally available in form of neutral fats, for example as triacylglycerides, or polar lipids such as, for example, phosphatidylcholine, phosphatidylethanolamine or phosphatidylinositol.

However, for the purpose of the present invention, the terms PUFA, n-3 fatty acid or n-3 active substances are understood to be all possible forms in which the corresponding fatty acids can exist, i.e. as free fatty acids as well as esters, triglycerides, phospholipids or other derivatives. All these substances are summarized in the following text and the terms are used synonymously. Furthermore, the PUFAs can be converted and concentrated by means of chemical or biocatalytic transesterification, for example with the help of suitable enzymes (lipases), before or after isolation from the culture.

The isolation of PUFAs from the fermented microorganisms or medium and the analysis of the fatty acid spectrum is carried out using common procedures known to the person skilled in the art [Wanasundara, U. N., Wanasundara, J., Shahidi, F., Omega-3 fatty acid concentrates: a review of production technologies, Seafoods—Quality, Technology and Nutraceutical Applications, 2002, pp. 157-174].

Cell harvest was carried out by centrifugation after 48 h of cultivation. The cells were subsequently freeze dried and the dry biomass determined. Cell digestion and fatty acid determination was carried out by means of 2 hour long heat treatment in 10% methanolic hydrochloric acid at 60° C. (under stirring). The esters were analyzed in a gas chromatograph to determine the fatty acid composition (Wanasundara, U. N., Wanasundara, J., Shahidi, F., Omega-3 fatty acid concentrates: a review of production technologies, Seafoods—Quality, Technology and Nutraceutical Applications, 2002, pp. 157-174).

TABLE 1

Influence of different salt contents on fermentation parameters

|  | Total salt content of sea water (ca. %) | NaCl in relation to sea water ca. g | Time (h) | DBM (g/L) | DHA/ DBM (%) | DHA quantity (g/L) | DHA space-time yield (g/L × d) |  |
| --- | --- | --- | --- | --- | --- | --- | --- | --- |
| Medium 1* | 50 | 15 | 48 | 25.4 | 16.6 | 4.20 | 2.11 | ⎫ |
| Medium 1.1 | 37.5 | 11.25 | 48 | 23.7 | 16.3 | 3.87 | 1.94 | ⎬ CE |
| Medium 1.2 | 25 | 7.5 | 48 | 22.5 | 18.9 | 4.26 | 2.13 | ⎭ |
| Medium 1.3 | 12.5 | 3.75 | 48 | 19.9 | 21.2 | 4.22 | 2.11 |  |
| Medium 1.4 | 5 | 1.5 | 48 | 21.0 | 23.9 | 5.02 | 2.51 |  |
| Medium 2* | 0 | 0 | 48 | 17.2 | 19.0 | 3.25 | 1.63 |  |

Figure 1:
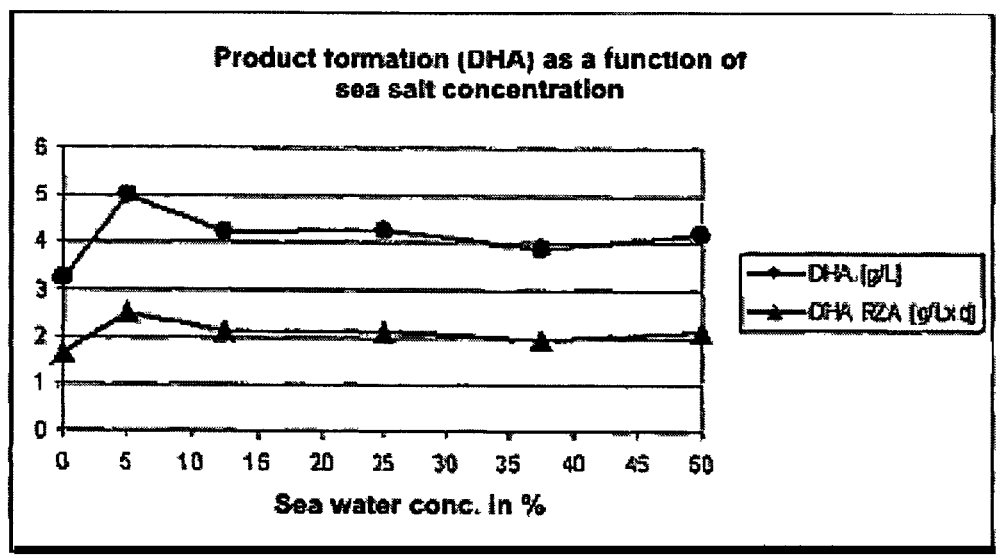
FIG. 1 shows the production of DHA in dependence of the salt concentration. The maximum in the range according to the invention is clearly visible (data from example 1).
Figure 2:
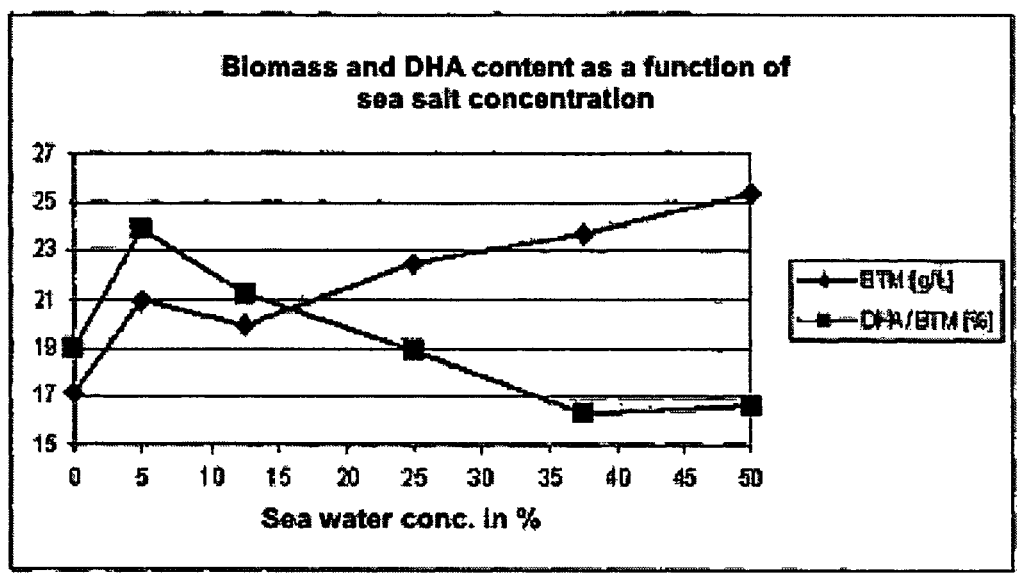

*Average values from two experiments, respectively.
DBM: Dry biomass;
DHA/DBM: wt % DHA (docosahexaenoic acid) per unit of weight DBM;
g/L × d space-time yield in grams per liter per day;
h: hour,
CE: comparative example FIG. 2 shows biomass and DHA content in dependence of the salt concentration. The maximum in the range according to the invention is also clearly visible in this case (data from example 1).

The fermentation medium forming the basis for the method according to the invention is described hereinafter by way of some examples. The fermentation medium as well as the invention is, however, not limited to these examples.

EXAMPLE 1

Influence of Different Salt Quantities in the Medium on the Production of PUFA by *Ulkenia* sp. SAM 2179

SAM 2179 strain (*Ulkenia* sp. BP-5601; WO9803671) was cultivated in 50 ml medium in 300 ml Erlenmeyer flasks with a baffle (temperature: 28° C., shaking rate: 150 rpm).
Medium 1: DH1 Medium

| Glucose monohydrate (g/L): | 56.25 |  |
| --- | --- | --- |
| Yeast extract (g/L): | 12.5 | [Difco] |
| Tropic Marin (g/L): | 16.65 | [Dr. Biener GmbH, Wartenberg, Germany] | pH value set to 6.0 with HCl

Medium 2: DH2 Medium (Without Salt)

| Glucose monohydrate (g/L): | 56.25 |  |
| --- | --- | --- |
| Yeast extract (g/L): | 12.5 | [Difco] | pH value set to 6.0 with HCl

The salts of medium 1 (Tropic Marin) were used in the following concentrations: 1× (medium 1), 0.75× (medium 1.1), 0.5× (medium 1.2), 0.25× (medium 1.3) and 0.1× (medium 1.4).

TABLE 2

Influence of different salt contents on the fatty acid spectrum

|  | 14:0 (%) | 15:0 (%) | 16:0 PA (%) | 22:5 DPAω6 (%) | 22:6 DHAω3 (%) | Other fatty acids (%) |  |
| --- | --- | --- | --- | --- | --- | --- | --- |
| Medium 1* | 2.9 | 3.7 | 32.2 | 10.2 | 45.7 | 5.5 | ⎫ |
| Medium 1.1 | 2.6 | 3.8 | 31.8 | 10.4 | 45.2 | 6.2 | ⎬ CE |
| Medium 1.2 | 2.0 | 3.6 | 29.5 | 11.2 | 47.4 | 6.3 | ⎭ |
| Medium 1.3 | 2.0 | 3.9 | 30.5 | 10.8 | 46.3 | 6.5 |  |
| Medium 1.4 | 2.6 | 4.8 | 32.4 | 11.1 | 43.5 | 5.6 |  |
| Medium 2* | 2.2 | 8.2 | 25.4 | 12.0 | 46.4 | 6.0 |  |

*Average values from two experiments, respectively.
14:0 myristic acid;
15:0 pentadecanoic acid;
16:0 palmitic acid;
DPAω6: docosapentaenoic acid (omega6);
DHAω3: docosahexaenoic acid (omega3)

The fermentation of *Ulkenia* sp., SAM 2179 strain, for different concentrations of Tropic Marin, starting from a sea water salt content of about 50% to 0%, shows that the biomass has a tendency to decrease with decreasing salt content in the medium. The fermentation at a low salt content of about 5% of sea water, however, surprisingly represents a significant exception. Here, the biomass production trend surprisingly features an intermediate maximum where higher values are attained again. In addition, the proportion of the predominant fatty acid DHA in the dry biomass increases with decreasing hydrochloric acid concentration and has its highest value also at 5% of the sea water salt content, decreasing again for even lower salt content. For the space-time yield of the essential PUFA DHA, this results in a maximum at a sea water salt content of about 5% (see Table 1). This maximum leads to an increase of the DHA space-time yield of more than 15%. The proportion of DHA for a sea water salt content of about 5% is, in relation to the overall fatty acid spectrum, slightly lower than for higher or lower salt contents (see Table 2), but the overall productivity for DHA and fatty acids or oil in general is, however, at its highest level at precisely this point (see Table 1). The low salt medium being the object of the present invention was developed based on these surprising results.

EXAMPLE 2

Production of PUFA Using *Ulkenia* sp. SAM 2179 in Different Fermentation Media

SAM 2179 strain was cultivated in 50 ml medium in 300 ml Erlenmeyer flasks with a baffle (temperature: 28° C., shaking rate: 150 rpm).

Medium 1: DH1 Medium

| | | |
|---|---|---|
| Glucose monohydrate (g/L): | 56.25 | |
| Yeast extract (g/L): | 12.5 | [Difco] |
| Tropic Marin (g/L): | 16.65 | [Dr. Biener GmbH, Wartenberg, Germany] | pH value set to 6.0 with HCl

Medium 2: DH2 Medium (Without Salt):

| | | |
|---|---|---|
| Glucose monohydrate (g/L): | 56.25 | |
| Yeast extract (g/L): | 12.5 | [Difco] | pH value set to 6.0 with HCl

Medium 3: DH3 Medium (With Salt Supplement Without Sodium and Without Chloride Addition):

| | | |
|---|---|---|
| Glucose monohydrate (g/L): | 56.25 | |
| Yeast extract (g/L): | 12.5 | [Difco] |
| Magnesium sulfate (g/L): | 1 | |
| Calcium carbonate (g/L) | 1 | |
| Potassium phosphate (g/L) | 1 | | pH value set to 6.0 with $H_2SO_4$

Cell harvest was carried out by centrifugation 48 h after cultivation. The cells were subsequently freeze dried and the dry biomass determined. Cell digestion and fatty acid determination was carried out by means of 2 hour long heat treatment in 10% methanolic hydrochloric acid at 60° C. (under stirring). The esters were analyzed in a gas chromatograph to determine the fatty acid composition.

The low salt medium without sodium and without chloride addition according to the invention was first used in the fermentation at a concentration of about 10% of the sea water salt content (medium 3). The biomasses obtained therewith are slightly lower in comparison with fermentations using about 50% sea water salt content, the DHA content per dry biomass is however larger, thus surprisingly leading to overall equal or even increased space-time yields (see Table 3). This is of considerable advantage for a later processing of the biomass to obtain DHA. Surprisingly, it was therefore shown that it is possible to advantageously completely dispense with the addition of sodium and/or chloride (the main salts in sea water) for the fermentation.

EXAMPLE 3

Influence of Different Salt Quantities in the Medium Without Sodium and Without Chloride Addition on the Production of PUFA by *Ulkenia* sp. SAM 2179

SAM 2179 strain was cultivated in 50 ml medium in 300 ml Erlenmeyer flasks with a baffle (temperature: 28° C., shaking rate: 150 rpm).

Medium 3: DH3 Medium (With Salt Supplement Without Sodium and Without Chloride Addition)

| | | |
|---|---|---|
| Glucose monohydrate (g/L): | 56.25 | |
| Yeast extract (g/L): | 12.5 | [Difco] |
| Magnesium sulfate (g/L): | 1 | |
| Calcium carbonate (g/L) | 1 | 1X salts |
| Potassium phosphate (g/L) | 1 | | pH value set to 6.0 with $H_2SO_4$

The salts of medium 3 were used in the following concentrations: 10× comprising 10 g/L each, 2× comprising 2 g/L each, 1× comprising 1 g/L each, 0.5× comprising 0.5 g/L each or 0.25× comprising 0.25 g/L each.

Cell harvest was carried out by centrifugation after 48 h of cultivation. The cells were subsequently freeze dried and the dry biomass determined. Cell digestion and fatty acid determination was carried out by means of 2 hour long heat treatment in 10% methanolic hydrochloric acid at 60° C. (under stirring). The esters were analyzed in a gas chromatograph to determine the fatty acid composition.

TABLE 3

Influence of different salt contents on fermentation parameters

| | Total salt content of sea water ca. % | NaCl in relation to sea water ca. g | Time (h) | DBM (g/L) | DHA/ DBM (%) | DHA quantity (g/L) | DHA space-time yield (g/L × d) | |
|---|---|---|---|---|---|---|---|---|
| Medium 1* | 50 | 15 | 48 | 25.4 | 16.6 | 4.20 | 2.11 | Comparative example |
| Medium 2* | 0 | 0 | 48 | 17.2 | 19.0 | 3.25 | 1.63 | |
| Medium 3** | 10 | 0 | 48 | 22.7 | 18.9 | 4.29 | 2.14 | |

*Average values from two experiments, respectively.
**Average values from three experiments, respectively.

TABLE 4

Influence of different salt contents on fermentation parameters

|  | Total salt content of sea water ca. % | NaCl in relation to sea water ca. g | Time (h) | DBM (g/L) | DHA/ DBM (%) | DHA quantity (g/L) | DHA space-time yield (g/L × d) |  |
| --- | --- | --- | --- | --- | --- | --- | --- | --- |
| Medium 3 (10X) | 100 | 0 | 48 | 32.5 | 12.5 | 4.05 | 2.03 | Comparative example |
| Medium 3 (2X) | 20 | 0 | 48 | 23.8 | 20.3 | 4.82 | 2.41 |  |
| Medium 3 (1X)** | 10 | 0 | 48 | 22.7 | 18.9 | 4.29 | 2.14 |  |
| Medium 3 (0.5X) | 5 | 0 | 48 | 22.7 | 21.2 | 4.82 | 2.41 |  |
| Medium 3 (0.25X) | 2.5 | 0 | 48 | 21.2 | 19.7 | 4.18 | 2.09 |  |

**Average values from three experiments, respectively.

Determination of the optimal salt concentration of the fermentation medium without sodium and without chloride addition was carried out by fermenting the microorganism *Ulkenia* sp. 2179 strain in the abovementioned medium with different salt concentrations. In this case, the DHA content per dry biomass was again the highest for a salt content of 5% of sea water (see also example 1). Productivity expressed as space-time yield also has an optimal value at this salt content (see Table 4).

EXAMPLE 4

Production of PUFA Using *Schizochytrium* SR21 Strain (*Schizochytrium* sp., MYA-1381; EP0823475) in Different Fermentation Media

*Schizochytrium* SR21 strain was cultivated in 50 ml medium in 300 ml Erlenmeyer flasks with a baffle (temperature: 28° C., shaking rate: 150 rpm).

Medium 1: DH1 Medium

| Glucose monohydrate (g/L): | 56.25 |  |
| --- | --- | --- |
| Yeast extract (g/L): | 12.5 | [Difco] |
| Tropic Marin (g/L): | 16.65 | [Dr. Biener GmbH, Wartenberg, Germany] | pH value set to 6.0 with HCl

Medium 2: DH2 Medium (Without Salt)

| Glucose monohydrate (g/L): | 56.25 |  |
| --- | --- | --- |
| Yeast extract (g/L): | 12.5 | [Difco] | pH value set to 6.0 with HCl

Medium 3: DH3 Medium (With Salt Supplement Without Sodium and Without Chloride Addition)

| Glucose monohydrate (g/L): | 56.25 |  |
| --- | --- | --- |
| Yeast extract (g/L): | 12.5 | [Difco] |
| Magnesium sulfate (g/L): | 1 |  |
| Calcium carbonate (g/L) | 1 |  |
| Potassium phosphate (g/L) | 1 |  | pH value set to 6.0 with $H_2SO_4$

Cell harvest was carried out by centrifugation after 48 h of cultivation. The cells were subsequently freeze dried and the dry biomass determined. Cell digestion and fatty acid determination was carried out by means of 2 hour long heat treatment in 10% methanolic hydrochloric acid at 60° C. (under stirring). The esters were analyzed in a gas chromatograph to determine the fatty acid composition.

TABLE 5

Influence of different salt contents on fermentation parameters

|  | Total salt content of sea water ca. % | NaCl in relation to sea water ca. g | Time (h) | DBM (g/L) | DHA/ DBM (%) | DHA quantity (g/L) | DHA space-time yield (g/L × d) |  |
| --- | --- | --- | --- | --- | --- | --- | --- | --- |
| Medium 1 SR 21 | 50 | 15 | 48 | 27.1 | 13.7 | 3.61 | 1.81 | Comparative example |
| Medium 2 SR 21 | 0 | 0 | 48 | 19.5 | 18.2 | 3.56 | 1.78 |  |
| Medium 3 SR 21 | 10 | 0 | 48 | 22.3 | 18.7 | 4.17 | 2.09 |  |

TABLE 6

Influence of different salt contents on the fatty acid spectrum

|  | 14:0 (%) | 15:0 (%) | 16:0 PA (%) | 22:5 DPAω6 (%) | 22:6 DHAω3 (%) | Other fatty acids (%) |  |
| --- | --- | --- | --- | --- | --- | --- | --- |
| Medium 1 SR 21 | 3.5 | 3.3 | 43.4 | 7.5 | 37.5 | 4.8 | Comparative example |
| Medium 2 SR 21 | 3.5 | 5.3 | 43.1 | 7.4 | 36.5 | 4.2 |  |
| Medium 3 SR 21 | 3.5 | 4.1 | 44.4 | 7.1 | 36.1 | 4.8 |  |

The low salt medium described in the invention also leads to an optimization of the production of PUFA in the case of other organisms belonging to *Labyrinthulomycota*. It is thus possible to ferment the microorganism *Schizochytrium* sp. SR21 strain in low salt medium without salt and without chloride addition. In this case, the DHA content related to the dry mass also has an optimum value for a salt content of 10% of sea water. Furthermore, an even stronger effect on the space-time yield of DHA and, with it, on the fermentation productivity is manifested herein. The DHA content related to the overall fatty acid spectrum is also slightly reduced in this case (see Table 6), although without affecting a surprisingly high space-time DHA yield (see Table 5). The low salt medium on which the present invention is based leads to a general production increase of PUFAs for different members of the *Labyrinthulomycota*.

The invention claimed is:

1. A method for cultivating microorganisms of the order *Thraustochytriales*, wherein the microorganisms are cultivated in a fermentation medium characterized in that the sum of the weight fractions of sodium and chloride ions is less than 1.75 g/L and that the total salt content of the fermentation medium is less than 3.5 g/L, and wherein during cultivation the microorganisms bring forth a production of more than 10 wt % DHA per dry biomass; and
    characterized in that the microorganism is selected from the group consisting of *Ulkenia* sp. SAM 2179 and *Schizochytrium* sp. SR 21.

2. The method according to claim 1, wherein up to 3 g/L $CaCO_3$ are added to the fermentation medium prior to and/or during cultivation.

3. The method according to claim 1, wherein the microorganisms bring forth a production of more than 14% DHA per dry biomass.

4. The method according to claim 1, wherein the microorganisms bring forth a production of more than 5% DPA per dry biomass.

5. The method according to claim 1, characterized by the use of the fermentation medium, the total salt content of which is in the range <8% of the salt content of sea water, the salt content of seawater being 32-35 g/L and a sodium and chloride content of 90-95%.

6. The method according to claim 1, characterized in that the total sodium content of the fermentation medium is less than 150 mg/L.

7. The method according to claim 1, characterized in that the total chloride content of the fermentation medium is less than 250 mg/L.

8. The method according to claim 1, characterized in that the fermentation medium comprises glucose, yeast extract, magnesium sulfate, calcium carbonate and potassium phosphate.

9. The method according to claim 1, characterized in that the fermentation medium comprises glucose, corn steep liquor, magnesium sulfate, calcium carbonate and potassium phosphate.

10. The method according to claim 8, characterized in that the fermentation medium comprises magnesium sulfate, calcium carbonate and potassium phosphate at less than 3 g/L each.

11. The method according to claim 1, characterized in that the fermentation medium has a pH value of between 3 and 10.

12. The method according to claim 1, characterized in that the cultivation takes place between 10° C. and 40° C.

13. The method according to claim 1, characterized in that the cultivation takes place for 1 to 10 days.

\* \* \* \* \*